United States Patent [19]

Ligon et al.

[11] Patent Number: 4,605,397
[45] Date of Patent: Aug. 12, 1986

[54] APPARATUS FOR SUPPORTING AND MANAGING A MEDICAL PIG TAIL TYPE FLUID INFUSION DEVICE

[76] Inventors: Kathy D. Ligon; Marcia J. Hoovler, both of 6741 A-1 Six Forks Rd., Raleigh, N.C. 27609

[21] Appl. No.: 694,019

[22] Filed: Jan. 23, 1985

[51] Int. Cl.[4] .............................................. A61M 5/00
[52] U.S. Cl. .................................... 604/179; 604/174; 128/DIG. 26
[58] Field of Search ............................... 604/174–180; 128/DIG. 26

[56] References Cited

U.S. PATENT DOCUMENTS

| | | | |
|---|---|---|---|
| 2,727,512 | 12/1955 | Muller | 128/DIG. 26 |
| 2,735,432 | 2/1956 | Hudson | 128/DIG. 26 |
| 2,831,487 | 4/1958 | Tafilaw | 128/DIG. 26 |
| 3,568,679 | 3/1971 | Reif | 604/180 |
| 3,630,195 | 12/1971 | Santomieri | 604/180 |
| 3,696,920 | 10/1972 | Lahay | 128/DIG. 26 |
| 4,029,103 | 6/1977 | McConnell | 128/DIG. 26 |
| 4,316,461 | 2/1982 | Marais et al. | 604/179 |
| 4,453,933 | 6/1984 | Speaker | 604/179 |

Primary Examiner—Dalton L. Truluck
Assistant Examiner—Michelle N. Lester
Attorney, Agent, or Firm—Mills and Coats

[57] ABSTRACT

The present invention entails an apparatus for receiving and holding a medical fluid infusion device of the type having a main patient feed line that directs fluid to and into a patient and which further includes a plurality of feeding pig tails that branch and extend from the main patient feed line. In order to maintain the pig tails in an orderly and untangled state, the apparatus of the present invention basically comprises a board type support structure that is provided with a series of spaced apart channels formed across the upper surface of the board and designed and adapted to receive and hold the respective pig tails and the main patient feed line.

6 Claims, 4 Drawing Figures

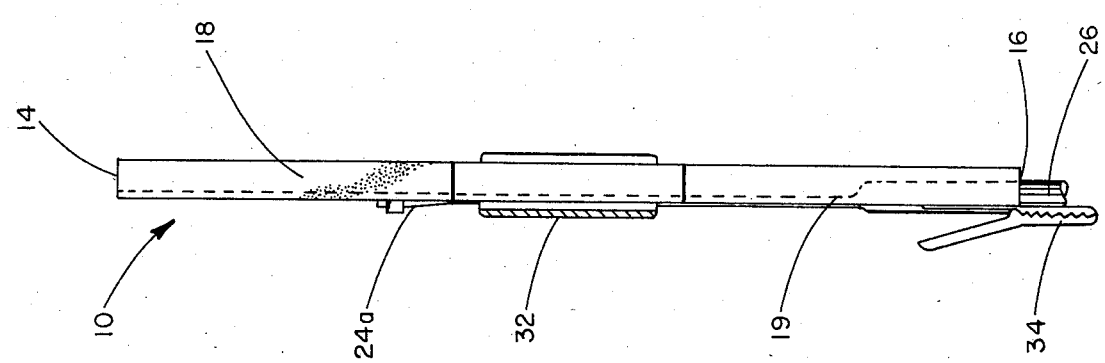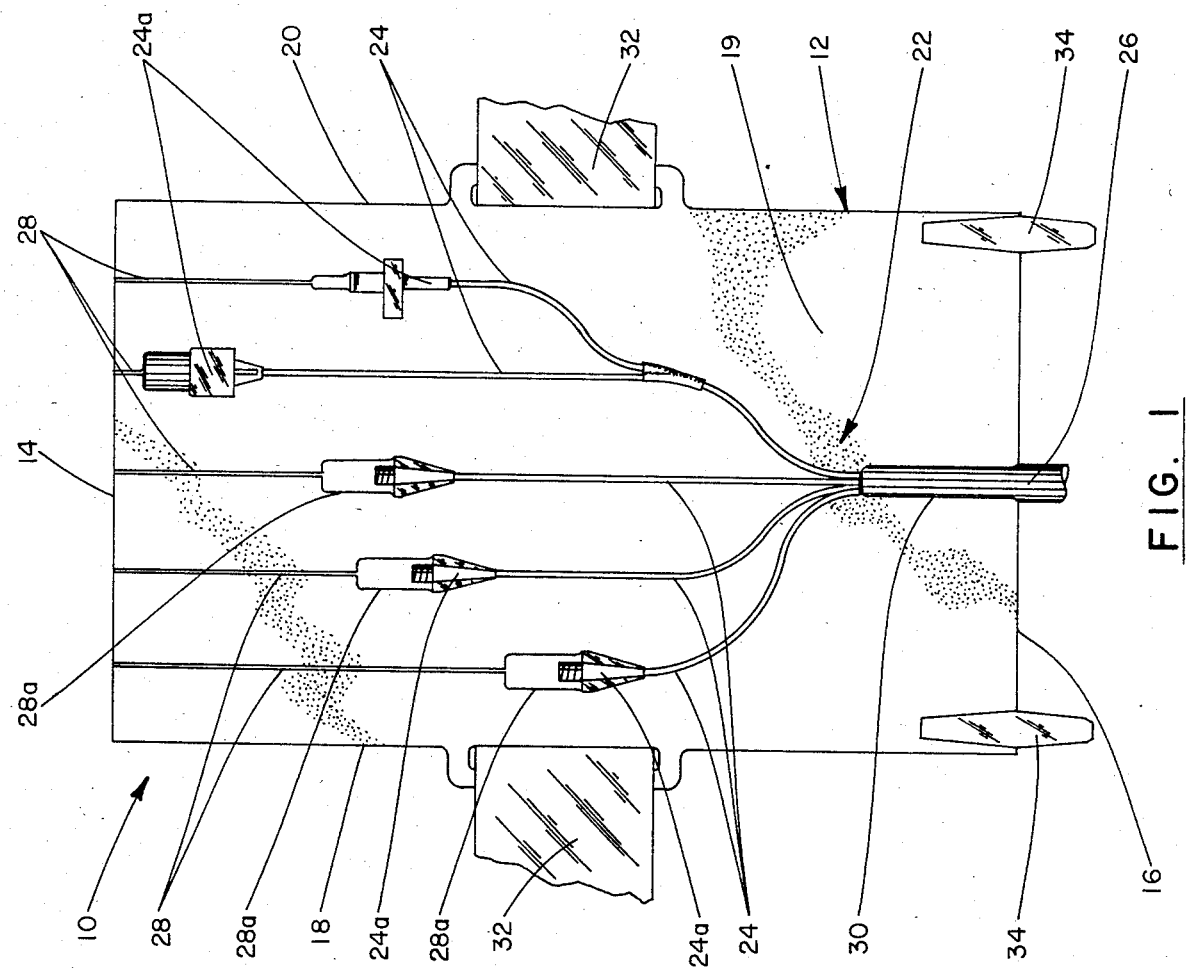

APPARATUS FOR SUPPORTING AND MANAGING A MEDICAL PIG TAIL TYPE FLUID INFUSION DEVICE

FIELD OF INVENTION

The present invention relates to medical apparatuses and more particularly to medical apparatus used in conjunction with fluid infusion devices.

BACKGROUND OF INVENTION

It is common practice to administer fluid solutions to a patient through a main feed line that has a series of pig tails that branch and extend therefrom. Typically the main feed line and pig tails are disposed bedside and adjacent the patient and the pig tails are connected to various fluid sources or to related inputs. Nurses who supervise and administer such infusion devices are well aware of the management problems associated with such. It is not uncommon for the various pig tails to become so tangled that it is impossible to determine which pig tail is connected to which fluid source or input. Consequently, in such a situation the attending nurse cannot visually see and determine which pig tail is connected to which input. This also leads to other problems. For example, in such a tangled state it is difficult to identify the proper end of a respective pig tail in order to appropriately connect the same to a new fluid source or input. In the end such intanglement causes the entire fluid infusion system to be difficult to manage and gives rise to substantial frustration and inefficiencies. Finally it must be remembered that these very infusion systems are being used to treat people who are often seriously ill and even find themselves in intensive care.

SUMMARY AND OBJECTS OF INVENTION

The present invention presents an apparatus specifically designed to receive and support such a fluid infusion device in an organized manner. In particular the apparatus of the present invention comprises a support structure having an upper surface that is provided with a series of channels formed therein across the entire board type structure. The series of channels enable one to press each of the respective pig tails therein and the channels are so formed such that the pig tail receiving channels merge to form a single channel to receive and accommodate the main patient feed line. The apparatus or support structure is also provided with attaching means that enables the same to be attached to the patient or to the patient's bed or any other structure therearound.

It is, therefore, an object of the present invention to provide an apparatus for holding and maintaining the medical fluid infusion device in an orderly and organized fashion.

Another object of the present invention resides in the provision of a board type structure for receiving and holding a pig tail type medical fluid infusion device.

Still a further object of the present invention resides in the provision of a board type structure of the character referred to above that is provided with channels formed in the upper surface thereof for receiving respective lines or pig tails of the fluid infusion device in such a manner that the respective lines or pig tails are held in spaced apart relationship across the board in such a manner that they are not easily susceptible to being entangled.

Another object of the present invention resides in the provision of an apparatus for receiving and holding a pig tail type medical infusion device that is simple in construction, easy to manufacture, and which is effective in holding and supporting various components of the infusion device in an organized fashion.

Other objects and advantage of the present invention will become apparent from a study of the following description and the accompanying drawings which are merely illustrative of such invention.

BRIEF DESCRIPTION OF DRAWINGS

FIG. 1 is a top plan view of the support structure of the present invention for receiving and holding a pig tail type medical infusion device.

FIG. 2 is a side elevational view of the apparatus shown in FIG. 1.

DETAILED DESCRIPTION OF INVENTION

Figure 3:
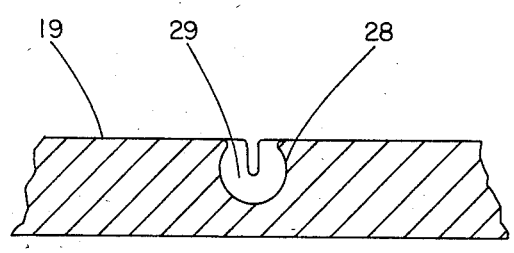
FIG. 3 is a fragmentary cross sectional view of a portion of the apparatus shown in FIGS. 1 and 2 which particularly illustrates a channel formed therein for receiving a line or component of such a pig tail type infusion device.

With reference to the drawings, the apparatus of the present invention is shown therein and indicated generally by the numeral 10. As referred to above, the apparatus 10 of the present invention is designed to receive and hold a pig tail type fluid infusion device indicated generally by the numeral 22. A detailed description of such a pig tail type infusion device will not be dealt with herein because such is not per se material to the present invention and further such devices are well known and appreciated in the art. However, briefly it should be pointed out that the pig tail type infusion device 22 includes a main patient feed line indicated by the numeral 26 which is adapted to channel and direct fluids to a patient via a catheter. Branching and extending from the main patient feed line 26 is a series of pig tails 24 with each pig tail having a connector 24a secured to the remote end thereof. The pig tail type fluid infusion device 22 is designed such that the respective connectors 24a can be connected to various fluid sources and inputs in accordance with the prescribed treatment for a patient being treated with such. A typical pig tail type fluid infusion device would be one such as manufactured and sold by Edwards Laboratories, Inc., of Anasco, Puerto Rico, and termed a "Thermodilution Venous Infusion Port Catheter."

Referring back to the present invention and apparatus 10, it is seen that the same basically comprises a board type structure indicated generally by the numeral 12. It should be pointed out that board type structure 12 could be constructed of plastic, Styrofoam, rubber or any other suitable material.

Viewing board structure 12, it is seen that the same includes a pair of opposed ends 14 and 16, a pair of opposed sides 18 and 20, and an upper surface 19.

Formed in the upper surface of board structure 12 is a series of channels that are specifically designed to accept and receive the pig tail type fluid infusion device 22. In particular the channels formed in the upper surface 19 of board 12 includes a series of pig tail channels 28 that are specifically designed to receive each of the pig tails 24 forming a part of the pig tail type infusion device 22. It is noted that pig tail channels 28 actually begin about end 14 of board type structure 12 and extend towards the opposite end 16 in parallel relationship. About an intermediate portion of the board type structure 12, the respective pig tail channels 28 merge inwardly to form a main feed line channel 30 that extends to and through end 16 of the board type structure 12 and which is adapted to receive and hold the main patient feed line 26 of the pig tail type infusion device 22.

Figure 4:
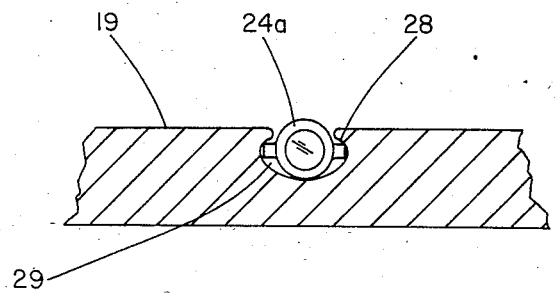
FIG. 4 is a cross sectional view similar to FIG. 3 except that the channel is shown receiving and holding an element of the pig tail type infusion device.

Respective channels 28 include an inner resilient liner 29 that is particularly illustrated in FIG. 3. Liner 29 is formed of a generally soft resilient foam-like material and includes a U-shaped opening formed therein. The presence of liner 29 enables the respective lines and components of the pig tail type fluid infusion device 22 to be easily and conveniently inserted into the channels formed in the upper surface 19 of the board 12. Note in FIG. 4 there is shown a connector end 24a inserted and held within a particular formed channel.

As particularly illustrated in FIG. 1, the respective pig tail channels 28 include an enlarged channel section 28a for receiving the respective connectors 24a of the pig tails 24. The enlarged channels 28a are particularly disposed intermediately about the board and spaced inwardly from end 16 in order that the lines associated with the various inputs and solution sources can also be secured within the respective pig tail channels 28 if so desired.

The board type structure 12 of the present invention is designed such that it can be attached to the bed or any other structure in the vicinity of the patient, including the patient. In this regard board 12 includes a strap attachment 32 as well as a pair of alligator clips 34.

In use the board type structure 12 of the present invention is secured in close vicinity of the patient being treated and is secured such that the upper surface 19 thereof is in clear view of the attending nurses and doctors. After the pig tail type fluid infusion device 22 has been appropriately inserted into the respective channels formed about the upper surface 19 of the board 12, as viewed in FIG. 1, then the respective connectors 24a can be connected to various fluid sources and to other associated inputs. Once this has been accomplished, it is seen that the various pig tails and any lines connected thereto are maintained in an orderly and untangled fashion. As such the attending nurses and doctors can actually see which inputs are connected to which pig tails 24 and this itself enables the various connectors 24a to be connected and disconnected in a very efficient and orderly manner without any accompanying confusion as to which connector 24a is connected to which input or fluid source.

Therefore, it is appreciated from the foregoing discussion that the present invention presents a very useful apparatus for supporting and maintaining such fluid infusion devices in an orderly and untangled manner.

The present invention may, of course, be carried out in other specific ways than those herein set forth without departing from the spirit and essential characteristics of the invention. The present embodiments are, therefore, to be considered in all respects as illustrative and not restrictive, and all changes coming within the meaning and equivalency range of the appended Claims are intended to be embraced therein.

What is claimed is:

1. A medical infusion management board for receiving and holding a fluid infusion line assembly having a main feed line and a plurality of pig tails that branch and extend therefrom and which are operative to connect to a series of different fluid sources for channeling the respective fluids into said main feed line and on into said patient, said medical infusion management board comprising:
    A. a board type support structure having an upper surface and opposed first and second ends;
    B. main channel means formed in the upper surface of said board type support structure for receiving and holding said main feed line of said pig tail type fluid infusion line assembly;
    C. said main channel means comprising a channel formed in the upper surface of said board type support structure and extending from a first end of said board type support structure to an intermediate area thereof;
    D. pig tail channel means formed in the upper surface of said board type support structure for receiving and holding said pig tails of said fluid infusion line assembly for maintaining the pig tails in spaced apart relationship about said board type support structure;
    E. said pig tail channel means including a plurality of separate, distinct and laterally spaced pig tail receiving channels formed across said board type support structure about the upper surface thereof with the respective pig tail channels extending in spaced apart relationship from said second end towards the intermediate area of said board type support structure and wherein said pig tail channels come together and merge with said main channel at the intermediate area of said board type support structure; and
    F. means for engaging and retaining said main feed line and said pig tails within the respective channels formed in said board type support structure such that said pig tails are maintained in spaced apart relationship in order that they may be freely and conveniently spaced and discussed to various inputs.

2. The medical infusion management board of claim 1 wherein said main channel and said pig tail channels extend completely through the first and second ends of said board type support structure so as to define a series of side channel openings formed about the first and second ends of said board type support structure.

3. The medical infusion management board of claim 1 wherein respective channels formed in said board type support structure include a relatively soft resilient liner with a U-shaped cutout formed therein that enables respective lines of the fluid infusion line assembly to be inserted within the U-shaped resilient liner and held within the respective channels.

4. The medical infusion management board of claim 3 wherein respective pig tails are provided with connector means formed about the remote ends thereof and wherein each of said formed pig tail channels includes an enlarged channel section appropriately spaced on said board type support structure for receiving and holding said connector means of the respective pig tails.

5. The medical infusion management board of claim 4 wherein said board is provided with connector means for connecting the same in close vicinity to the patient that is receiving fluids through the fluid infusion line assembly.

6. A method of managing a medical fluid infusion system of the type having a main patient feed line and a plurality of pig tails branching and extending therefrom with respective pig tails having a connector formed about the remote end thereof, said method comprising: forming a series of pig tail receiving channels in a board-type support structure such that said pig tail receiving channels extend from one edge of said support structure to an intermediate area thereof; merging said pig tail receiving channels about an intermediate area of said support structure and forming one main line receiving channel which extends from said merging pig tail receiving channels to the opposite edge of said support structure; and securing said fluid infusion system to said support structure by pressing the main patient feed line into said main line receiving channels and by pressing the plurality of pit tails into respective pig tail receiving channels.

* * * * *